United States Patent
Ward

(10) Patent No.: US 6,172,233 B1
(45) Date of Patent: *Jan. 9, 2001

(54) PROCESS FOR MAKING PAROXETINE

(75) Inventor: Neal Ward, Tonbridge (GB)

(73) Assignee: SmithKline Beecham plc, Brentford (GB)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/007,475

(22) Filed: Jan. 15, 1998

(30) Foreign Application Priority Data

Jan. 15, 1997 (GB) .................................................. 9700690

(51) Int. Cl.[7] .......................... C07D 211/02; C07D 211/60
(52) U.S. Cl. ........................... 546/185; 546/227; 546/228
(58) Field of Search ................................. 546/185, 225, 546/227, 228

(56) References Cited

U.S. PATENT DOCUMENTS

| | | | |
|---|---|---|---|
| 2,498,432 | 2/1950 | Lee | 546/217 |
| 3,912,743 | * 10/1975 | Christensen et al. | 546/185 |
| 4,007,196 | 2/1977 | Christensen et al. | 546/197 |
| 4,585,777 | 4/1986 | Lassen | 514/317 |
| 4,623,728 | * 11/1986 | Sarges | 546/236 |
| 5,258,517 | 11/1993 | Zepp | 546/240 |
| 5,661,162 | * 8/1997 | MacLeod et al. | 514/331 |
| 5,665,736 | 9/1997 | Foguet et al. | 514/321 |

FOREIGN PATENT DOCUMENTS

| | | |
|---|---|---|
| 300617 | 1/1989 | (EP) . |
| 374674 | 6/1990 | (EP) . |
| 96/36636 | 11/1996 | (WO) . |

OTHER PUBLICATIONS

Plati, et al., "Pyridindene Derivatives. III. Synthesis from Arecoline", *J. Org. Chem.* 22, pp. 261–265 (Mar., 1957).

\* cited by examiner

*Primary Examiner*—John Kight
*Assistant Examiner*—Raymond Covington
(74) *Attorney, Agent, or Firm*—Wayne J. Dustman

(57) ABSTRACT

Compounds of structure (2) are prepared by reaction of an arecoline analogue of structure(4) with an organometallic compound containing an X-substituted phenyl group, such as a compound of structure (3).

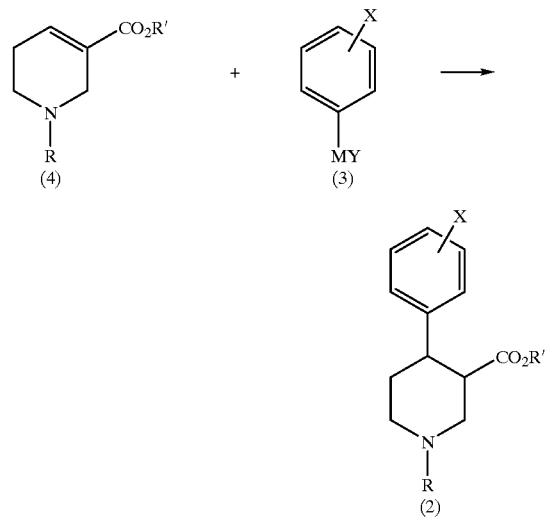

Suitably the compound of structure (3) is a Grignard reagent, where M is magnesium and Y is a halogen atom, or M may be a Group II metal and Y is a halogen atom or a second X-substituted phenyl group. When structure (3) is a Grignard reagent, the reaction is carried out either in a suitable non-ether solvent, typically a hydrocarbon or a non-reactive chlorinated hydrocarbon, or in a mixture of such a solvent with diethyl ether. Compounds of structure (2) are important intermediates in the preparation of inter alia paroxetine.

16 Claims, No Drawings

PROCESS FOR MAKING PAROXETINE

The present invention relates to a new process for preparing pharmaceutically active compounds and intermediates therefor.

Pharmaceutical products with antidepressant and anti-Parkinson properties are described in U.S. Pat. No. 3,912,743 and U.S. Pat. No. 4,007,196. An especially important compound among those disclosed is paroxetine.

This invention aims to overcome disadvantages in the existing processes for preparation of such compounds and so to provide alternative processes for their manufacture.

This invention has been developed on the basis that compounds of structure (1) and (2) below are valuable chemical intermediates useful for the manufacture of important medicinal products, for example paroxetine hydrochloride.

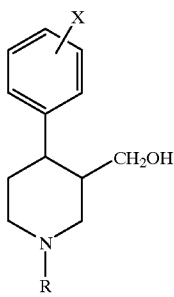

(1)

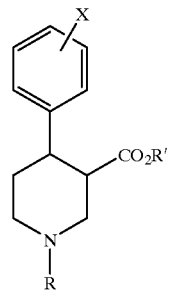

(2)

By reference to Example 4 of U.S. Pat. No. 4,007,196, paroxetine may be prepared from a compound of structure (1) in which R is methyl and X is 4-fluoro, that is 4-(4'-fluorophenyl)-3-hydroxymethyl-1-methylpiperidine, by replacing the hydroxymethyl group with 3,4-methylenedioxyphenoxymethyl, followed by demethylation, replacing the R=methyl group by hydrogen. In the same Example, 4-(4'-fluorophenyl)-3-hydroxymethyl-1-methyl piperidine is prepared by reduction of 4-(4'-fluorophenyl)-3-hydroxymethyl-1-methyl-1,2,3,6-tetrahydropyridine, which is in turn prepared from 4-(4'-fluorophenyl)-1-methyl-1,2,3,6-tetrahydropyridine, by reaction with formaldehyde.

U.S. Pat. No. 4,007,196 also discloses that compounds of structure (1) which are 4-(fluorophenyl)-3-hydroxymethyl-1-alkyl piperidines can be obtained by reduction of compounds of structure (2) which are 4-(fluorophenyl)-3-carboxymethoxy-1-alkyl piperidines. The latter are prepared using a literature procedure (J.T. Plati, A.K Ingerman and W Wenner, Journal of Organic Chemistry (1957) Volume 22 pages 261-265). Plati et al describe the reaction of the tetrahydropyridine arecoline with phenyl magnesium bromide in diethyl ether to prepare 1-methyl-3-carbomethoxy-4-phenyl piperidine (compound (2) where R and R' are methyl groups and X is a hydrogen atom).

EP-A-0219034 discloses an alternative method for the preparation of some 4-(substituted phenyl)-3-carboxyalkoxy-1-alkyl piperidines, and their reduction to 4-(substituted phenyl)-3-hydroxymethyl-1-alkyl piperidines.

Paroxetine is the (−) trans isomer of 4-(4'-fluorophenyl)-3-(3',4'-methylenedioxy-phenoxymethyl)-piperidine. The above described processes produce compounds of structure (1) as a mixture of enantiomers. Therefore conversion of compounds of structure (1) to useful pharmaceuticals will normally require a resolution stage.

The Plati et al procedure uses diethyl ether, which is a very flammable solvent and its use in large scale production is highly undesirable. However, we have found that other ether solvents conventionally used in Grignard reactions, such as tetrahydrofuran or diisopropyl ether result in little if any of the desired 1,4-conjugate addition product, as the major product arises from attack of the Grignard reagent on the ester grouping (so called 1,2-addition). We have also have found that the Plati procedure generates thick unstirrable gels and is unsuitable for large scale production of compounds of structure (2).

As a result, we have discovered that the Plati et al procedure used in U.S. Pat. No. 4,007,196 can be improved by use of other organometallic compounds in place of the Grignard reagent, or by varying the conditions under which a Grignard reagent is used, enabling the stirring problems to be overcome and the use of diethyl ether eliminated or significantly reduced.

Accordingly a first aspect of this invention provides a process for the preparation of a compound of structure (2)

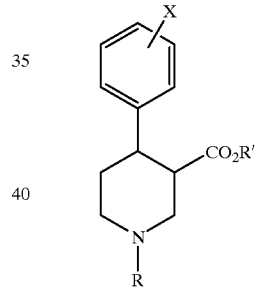

(2)

in which R and R' are independently an alkyl, aryl, or arylalkyl group, most suitably lower alkyl, and X is one or more of hydrogen, halogen (especially fluoro), hydroxy, alkoxy, nitro, nitrile, amino (optionally protected or substituted), trifluoromethyl, acyl, formyl, carboxyl or carboxyalkyl, which comprises reacting a compound of structure (4)

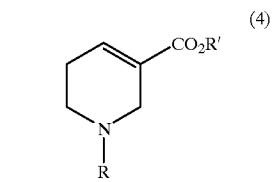

(4)

with an organometallic compound having one or more X-substituted phenyl groups, in a suitable organic solvent, provided that the solvent is not wholly diethyl ether when the organometallic compound is a Grignard reagent.

The organometallic compound may be any X-substituted phenyl derivative capable of undergoing a 1,4-conjugate to a compound of structure (4), such as a Grignard reagent, and X-substituted phenyl derivatives of Group II metals. For example, the organometallic compound may be a compound of structure (3)

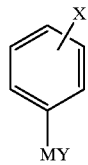

(3)

in which M is a Group II metal and Y is a halogen or an X-substituted phenyl group. Suitable compounds of structure (3) include Grignard reagents, in which case M is magnesium and Y is conveniently chlorine or bromine. The compound of structure (3) may also be a symmetrical molecule, where M represents for example a zinc atom and Y is a second X-substituted phenyl group.

When structure (3) represents a Grignard reagent the reaction is carried out either in a suitable non-ether solvent, or in a mixture of such a solvent with diethyl ether. Suitable non-ether solvents are those which are compatible with the reaction conditions for example those which do not react with Grignard reagents. Such solvents include hydrocarbons such as hexane or toluene, and unreactive chlorinated hydrocarbons such as dichloromethane.

Where it is desired to carry out the reaction in a non-ether solvent, the Grignard reagent of formula (3) may either be prepared in the chosen solvent, or prepared in an ether solvent and the ether subsequently removed by distillation and replaced by the chosen solvent. When employed in a non-ether solvent, a Grignard reagent of formula (3) may be partially or completely insoluble, but the resulting suspension is stirrable and compatible with large scale operation. When a mixture of diethyl ether and a suitable non-ether solvent is employed, a completely clear solution may be obtained, rendering the process particularly suitable for industrial scale operation.

By using the processes of this invention the reaction has been found to be more efficient, and the large excess of Grignard reagent specified by Plati (2 molar equivalents) can be significantly reduced without loss in yield. We have also found that the reaction is equally efficient if the order of addition of the reagents is reversed, i.e. the Grignard reagent is added to the tetrahydropyridine ester.

Compounds of structure (3) may be prepared by conventional procedures for Grignard reagents and the other organometallic compounds, starting from an appropriately X-substituted aromatic compound. Where the desired end product is paroxetine, an appropriately X-substituted aromatic compound would be 1-bromo-4-fluorobenzene.

Compounds of formula (4) may be prepared from the natural products guvacine, arecaidine or arecoline, by conventional methods, or by synthesis from other materials. A particularly convenient synthetic procedure involves the esterification, quaternisation and partial reduction of nicotinic acid [see for example Journal of Organic Chemistry (1955), volume 20, pages 1761–1765; Journal of Chemical Research (1983), volume 10, pages 2326–2342; Journal of Ph maceutical Sciences (1992), volume 81, pages 1015–1019; and references quoted therein].

(4)

Other methods for the preparation of compounds of structure (4) are given in Tetrahedron (1989) volume 45 pages 23–258, and Heterocycles (1990) volume 30 pages 885–896.

The compounds of structure (2) may be reduced to compounds of structure (1) by the general procedures disclosed in EP-A-0219934.

Compounds of structure (1) may be converted to an active compound disclosed in U.S. Pat. No. 3,912,743 or U.S. Pat. No. 4,007,196 using conventional procedures disclosed therein. Where appropriate or necessary, compounds of structure (1) may be resolved to obtain the (−)trans isomer using conventional reagents such a nitro tartranilic acid, as described in EP-A-0223334—see Example 5.

In particular, the compound of structure (1) in which X is 4-fluoro may be used to prepare paroxetine. The paroxetine is preferably obtained as the hydrochloride salt and most preferably as the hemihydrate of that salt, as described in EP-A-0223403.

The present invention includes within its scope the compound paroxetine, particularly paroxetine hydrochloride, especially as the hemihydrate, when obtained via any aspect of this invention, and any novel intermediates resulting from the described procedures.

The invention is illustrated by the following Examples:

Example 1

1-methyl-3-carbomethoxy-4-(4-fluorophenyl)-piperidine

A 2 molar solution of 4-fluorophenylmagnesium bromide in diethyl ether (5 ml, 2 molar equivalents) was diluted with toluene (5 ml) and heated under nitrogen until the ether had been removed. The resulting suspension was cooled to ca. −5° C. and treated with a solution of arecoline (0.78 g) in toluene (4.5 ml) over 15 minutes. The mixture was stirred at −5° C. for 1 hour, then quenched by the addition of a mixture of water (25 ml) and concentrated hydrochloric acid (3 ml). Analysis of the aqueous phase by HPLC showed that yield of cis/trans 1-methyl-3-carbomethoxy-4-(4-fluorophenyl)-piperidine was about 880 mg (70 %).

Example 2

1-methyl-3-carbomethoxy-4-(4-fluorophenyl)-piperidine

A 2 molar solution of 4-fluorophenylmagnesium bromide in diethyl ether (5 ml, 2 molar equivalents) was stirred at −5 to −10° C. under nitrogen, and a solution of arecoline (0.78 g) in toluene (5.0 ml) added over 15 minutes at −5° C. The clear solution was stirred at −5° C. for 1 hour, then quenched by the addition of a mixture of water (25 ml) and concentrated hydrochloric acid (3 ml). Analysis of the aqueous phase by HPLC showed that yield of cis/trans 1-methyl-3-carbomethoxy-4-(4-fluorophenyl)-piperidine was about 905 mg (72 %).

Example 3

1-methyl-3-carbomethoxy-4-(4-fluorophenyl)-piperidine

A 2 molar solution of 4-fluorophenylmagnesium bromide in diethyl ether (5 ml, 2 molar equivalents) was stirred at −5 to −10° C. under nitrogen, and a solution of arecoline (0.78 g) in dichloromethane (4.0 ml) added over 15 minutes at −5° C. The clear solution was stirred at −5° C. for 1 hour, then quenched by the addition of a mixture of water (25 ml) and concentrated hydrochloric acid (3 ml). Analysis of the aqueous phase by HPLC showed that yield of cis/trans 1-methyl-3-carbomethoxy-4-(4-fluorophenyl)-piperidine was about 950 mg (76 %).

Example 4

1-methyl-3-carbomethoxy-4-(4-fluorophenyl)-piperidine

A 2 molar solution of 4-fluorophenylmagnesium bromide in diethyl ether (3.5 ml, 1.4 molar equivalents) was stirred at −5 to −10° C. under nitrogen, and a solution of arecoline (0.78 g) in dichloromethane (4.0 ml) added over 15 minutes at −5° C. The clear solution was stirred at −5° C. for 1 hour, then quenched by the addition of a mixture of water (25 ml) and concentrated hydrochloric acid (3 ml). Analysis of the aqueous phase by HPLC showed that yield of cis/trans 1 ethyl-3-carbomethoxy-4-(4-fluorophenyl)-piperidine was about 965 mg (77 %).

Example 5

1-methyl-3-carbomethoxy-4-(4-fluorophenyl)-piperidine - reverse addition

A 2 molar solution of 4-fluorophenylmagnesium bromide in diethyl ether (3.5 ml, 1.4 molar equivalents) was added over 15 minutes to a stirred solution of arecoline (0.78 g) in dichloromethane (4.0 ml) at −5 to −10° C. under nitrogen. The clear solution was stirred at −5° C. for 1 hour, then quenched by the addition of a mixture of water (25 ml) and concentrated hydrochloric acid (3 ml). Analysis of the aqueous phase by HPLC showed that yield of cis/trans 1-methyl-3-carbomethoxy-4-(4-fluorophenyl)-piperidine was about 970 mg (77 %)

What is claimed is:

1. A process for industrial scale preparation of a compound of structure (2)

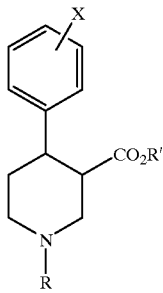

(2)

in which R and R' are independently selected from an alkyl, aryl, or arylalkyl group, X is fluorine which comprises reacting a compound of structure (4)

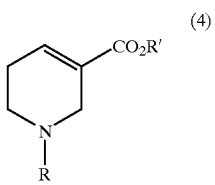

(4)

with an organometallic compound having one or more X-substituted phenyl groups, in a suitable organic solvent, provided that the solvent is not wholly an ether solvent when the organometallic compound is a Grignard reagent.

2. A process according to claim 1, in which the organometallic compound is a compound of structure (3)

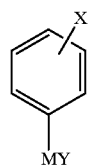

(3)

in which X is as defined in claim 1, M is a Group II metal and Y is a halogen or an X-substituted phenyl group.

3. A process according to claim 2, in which M is Zn and Y is a second X-substituted phenyl group.

4. A process according to claim 2, in which structure (3) is a Grignard reagent and the organic solvent is a non-ether solvent or a mixture of a non-ether solvent with diethyl ether.

5. A process according to claim 4, in which M is Mg and Y is Cl or Br.

6. A process according to claim 1, in which the solvent is a hydrocarbon or a non-reactive chlorinated hydrocarbon.

7. A process for the preparation of a 4-aryl-3-hydroxymethyl-piperidine of structure (1)

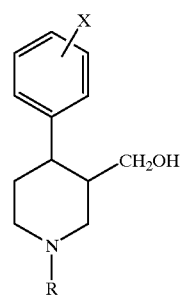

(1)

comprising converting a compound of structure (2) obtained by the process of claim 1 into a compound of structure (1).

8. A process for preparing paroxetine comprising obtaining a compound of structure (1) in which X is 4-fluoro by a process as claimed in claim 7, replacing the 3-hydroxymethyl group by a 3-(3,4-methylenedioxyphenyloxymethyl) group, and replacing the substituent R with a hydrogen atom.

9. A process according to claim 8, in which paroxetine is obtained as, or converted to, a hydrochloride salt.

10. A process according to claim 9, in which the paroxetine hydrochloride salt is obtained as the hemihydrate.

11. Paroxetine when prepared according to the process of claim 8.

12. Paroxetine hydrochloride when prepared according to the process of claim 9.

13. Paroxetine hydrochloride hemihydrate when prepared according to the process of claim 10.

14. A process according to claim 1, in which the solvent contains toluene.

15. A process according to claim 1, in which the solvent contains dichloromethane.

16. A process according to claim 7, wherein a reducing agent is used to convert the compound of structure (1) into a compound of structure (2).

* * * * *